United States Patent [19]

Hasty et al.

[11] Patent Number: 4,745,917
[45] Date of Patent: May 24, 1988

[54] THERAPEUTIC STOCKING

[75] Inventors: James H. Hasty, Glenview; Betsy C. Westlake, Palatine, both of Ill.

[73] Assignee: The Kendall Company, Boston, Mass.

[21] Appl. No.: 774,778

[22] Filed: Sep. 11, 1985

[51] Int. Cl.$^4$ ............................................. A61F 13/00
[52] U.S. Cl. ..................................................... 128/165
[58] Field of Search ..................... 66/178 A, 172 E; 361/42; 128/165, 525, 530

[56] References Cited

U.S. PATENT DOCUMENTS

| Re. 25,046 | 10/1961 | Knohl | 66/178 A |
| 2,883,842 | 4/1959 | Knohl | 66/178 A |
| 3,728,875 | 4/1973 | Hartigan | 128/165 |
| 3,889,494 | 6/1987 | Patience et al. | 66/178 |
| 4,172,456 | 10/1979 | Zens | 66/178 A |
| 4,513,940 | 4/1985 | Westlake | 128/165 |

Primary Examiner—Gregory E. McNeill
Attorney, Agent, or Firm—Powell L. Sprunger

[57] ABSTRACT

Appropriate compression profiles for stockings to manage venous disorders in the lower extremities of ambulatory individuals are defined. Three profiles are described for the treatment of three categories of venous disease: mild venous disease, superficial venous insufficiency, and deep venous insufficiency. The highest pressures are used to manage the most severe disorder. The stockings use large pressure gradients to provide support for microscopic hemodynamics and valvular function at each region of the leg without producing venous congestion. The large gradients also ensure the maintainence of graduated pressure for the general population with an acceptable number of stocking sizes. Reduced foot pressures are also utilized to enhance patient compliance while avoiding a tourniquet effect.

54 Claims, 3 Drawing Sheets

| COURSES | WALES | | | |
|---|---|---|---|---|
| | 22 | 20 | 22 | 20 |
| 6 | X | O | X | O |
| 5 | X | - | X | - |
| 4 | X | O | X | O |
| 3 | O | X | O | X |
| 2 | - | X | - | X |
| 1 | O | X | O | X |

FIG 3

STITCHES { KNIT X, TUCK O, FLOAT - }

COURSES { 1, 2, 3, 4, 5, 6 }

CLOSED VALVE
DIASTOLE II

FIG. 8b

INCOMPETENT FLOWS
SYSTOLE

FIG. 8c

INCOMPETENT VALVES
DIASTOLE I

↑ PROXIMAL

FIG. 9

↓ DISTAL

FIG. 10

MID THIGH —26%
38
30
32
36
CALF —50%
34
ANKLE —100%
40
FOOT —56%

FIG. 11

MID THIGH —30%
38
32
50
CALF —50%
36
34
ANKLE —100%
40
FOOT —60%

FIG. 12

MID THIGH —36%
38
32
60
CALF —55%
36
34
ANKLE —100%
40
FOOT —68%

4,745,917

THERAPEUTIC STOCKING

BACKGROUND OF THE INVENTION

The present invention relates to therapeutic stockings.

Therapeutic stockings which exert a compressive pressure against a patient's leg are known, and the problem of the definition of an appropriate compression stocking for the management of the venous system in the lower extremities has been a topic of discussion for many years. Various types of stockings and compression profiles have been used, but it has been unclear what the appropriate compression profile should be to deal with the enormous spectrum of venous disorders found in the ambulatory patient.

In the early experimental work of Sigel, Edelstein, Savitch, Hasty, and Felix (Arch. Surg., Vol. 110, February, 1975, pp 171-175), the appropriate pressure gradient was defined to optimally compress the lower extremity to produce the greatest increase in femoral vein flow velocity consistant with safety and practicality of hospital use of elastic stockings. However, this definition was directed to the prophylaxis of deep vein thrombosis during inactive recumbency. The definition of appropriate compression profiles for the management of venous difficulties in the lower extremities of ambulatory individuals is a totally different problem.

SUMMARY OF THE INVENTION

A principal feature of the present invention is the provision of improved therapeutic stockings.

The stockings of the present invention exert compressive pressures against the legs with a pressure profile which decreases from the ankle to the upper thigh.

A feature of the present invention is that the stockings define a pressure profile for use in patients having deep venous insufficiency in the legs.

Another feature of the invention is that the stockings define a pressure profile for patients having superficial venous insufficiency in the legs.

Yet another feature of the invention is that the stockings define a pressure profile for patients having mild venous disease in the legs.

A feature of the present invention is that the stockings provide a large pressure gradients for support of microscopic hemodynamics and valvular function at each region of the leg without producing venous congestion.

A further feature of the invention is that the large gradients of the stockings also insure the maintenance of graduated pressure for the general population with an acceptable number of stocking sizes.

Further features will become more fully apparent in the following description of the embodiments of this invention and from the appended claims.

DESCRIPTION OF THE PREFERRED EMBODIMENTS

A preferred knit construction for use with the stockings of the present invention is disclosed in connection with FIGS. 1-4. This knit construction is disclosed and claimed in U.S. Pat. No. 4,494,388, incorporated herein by reference.

Figure 1:
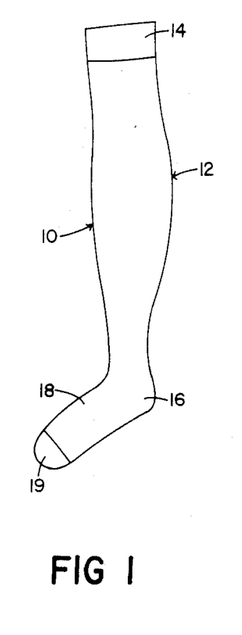
FIG. 1 is a plan view of a compression stocking which is illustrative of a knit construction utilized for the stockings of the present invention.

Turning now to the drawings, FIG. 1 illustrates a therapeutic anti-embolism stocking, generally designated 10, comprising a boot or leg portion 12 having a welt portion 14 at the upper end thereof, a heel portion 16, a foot portion 18, and a toe portion 19. The entire stocking, except for the welt portiion 14 and the toe portion 19, may be of fabric knit according to the present description. The welt, heel, and toe may be of conventional jersey knit.

Figure 2:
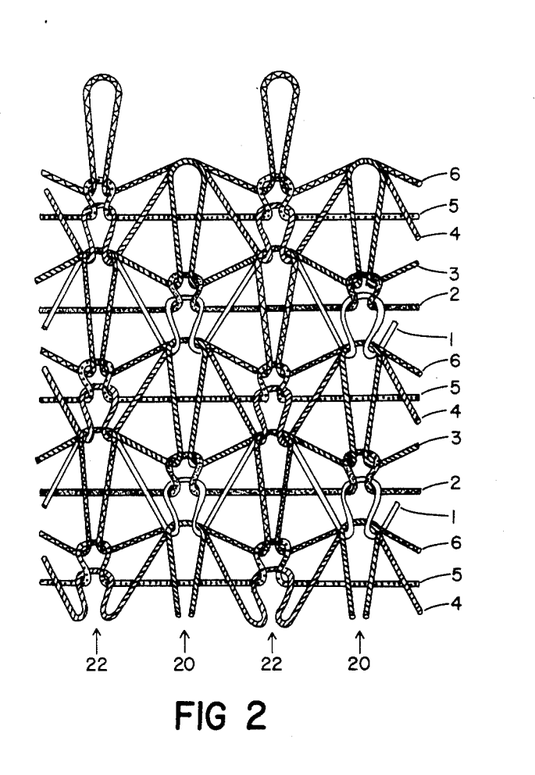
FIG. 2 is a diagrammatic representation of the front of a fabric comprising the knit construction for the stockings, showing the stitches.
Figure 3:
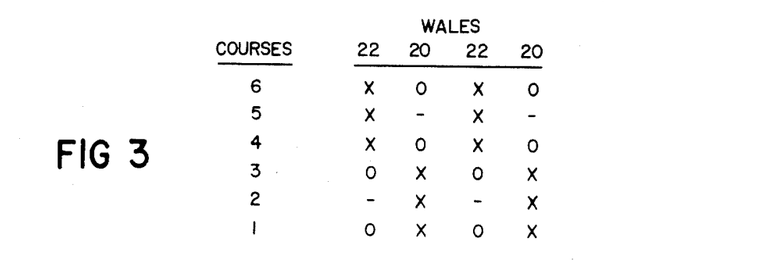
FIG. 3 is a schematic representation of the knit construction.
Figure 4:
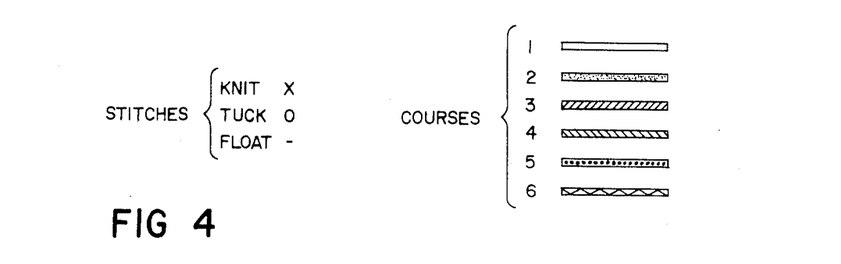
FIG. 4 is a legend showing coding and symbols used in FIGS. 2 and 3.

The fabric is a knit construction comprising a repeating six-course, two-wale pattern. As shown in FIGS. 2 and 3, the six courses (designated 1 through 6 respectively) repeat through the height of the stocking; the two wales (designated 20 and 22 respectively) repeat around the stocking circumference.

Courses 1, 3, 4 and 6 are a textured nylon yarn such as that sold by E. I. duPont; courses 2 and 5 are a bare or covered elastomeric yarn, such as duPont Lycra. Each course 1 comprises, from right to left as shown, alternating knit and tuck stitches. Courses 2 comprise alternating knit and float stitches; and courses 3 comprise alternating knit and tuck stitches. The knit stitches of courses 1, 2 and 3 lie in wales 20, i.e., are vertically aligned with each other in every other wale.

Each course 4 comprises, again from right to left as shown, alternating tuck and knit stitches, as does each course 6. Each course 5 comprises alternating float and knit stitches. The knit stitches of courses 4, 5 and 6 lie in wales 22, intermediate the wales 20 containing the knit stitches of courses 1, 2 and 3.

As previously stated, the first and third stitches of courses 1, 2 and 3 are all knit stitches and lie in wales 20. The first and third stitches of courses 1 loop the first and third stitches of courses 2; the first and third stitches of courses 2 loop the first and third stitches of courses 3; and the first and third stitches of courses 3 pass over the first and third stitches of course 5 (which are float stitches) and, with the first and third stitches of courses 4 and 6 (both of which are tuck stitches), loop the first and third stitches of the next repeat of course 1.

In wales 22, the second and fourth stitches of courses 1 pass over the second and fourth stitches (the float stitches) of courses 2; and the second and fourth stitches of both of courses 1 and 3 are tucked behind the loops formed by the second and fourth stitches (the knit stitches) of courses 4.

It will be seen that the pattern of courses 4-6 essentially repeats that of courses 1-3, except that it is offset one wale so that the wales 22 containing the knit stitches of courses 4-6 lie between wales 20 of the knit stitches of courses 1-3.

Thus, in wales 22, the second and fourth stitches of courses 4 (which are knit stitches) loop the second and fourth stitches of courses 5; and the second and fourth stitches of courses 5 loop the second and fourth stitches of courses 6. Further, the second and fourth stitches of courses 6 pass over the float stitches (the second and fourth stitches) of course 2 and, with the second and fourth stitches (both tuck stitches) of courses 1 and 3 of the next repeat, loop the second and fourth stitches of the next repeat of course 4.

In wales 20, the first and third stitches of courses 4 (both tuck stitches) pass over the first and third stitches (the float stitches) of courses 5, and the first and third stitches of both of courses 4 and 6 are tucked behind the loop formed by the first and third stitches (the knit stitches) of courses 1.

In wales 20, it will be seen that the knit stitches of courses 3 and the tuck stitches of courses 4, i.e., the stitches that pass over the float stitches of courses 5 of elastomeric yarn, have relatively long, free "legs" extending generally along the wales, as do the knit stitches of courses 6 and the tuck stitches of courses 1 (i.e., the stitches that pass over the float stitches of courses 2) in wales 22. This construction permits the fabric to stretch in a horizontal or circumferential direction (parallel to the courses 2, 5 of elastomeric yarn). Stretch in the vertical direction is provided largely by the tuck stitches, which as shown in FIG. 2 extend diagonally of the fabric when the fabric is relaxed.

When the fabric is in its relaxed condition, the number of courses and wales per inch at various regions of the stocking, and the circumference of one size stocking, typically are generally as shown in the following table.

TABLE

| Region | Circumference | Courses/Inch | Wales/Inch |
|---|---|---|---|
| Ankle | 4¾ in. | 40–50 | 80–100 |
| Calf | 8 in. | 30–40 | 50–60 |
| Thigh | 11 in. | 25–30 | 35–45 |

When worn, the stocking typically will stretch lengthwise (i.e., along the wales) some 20%–30% in the ankle region, about 50% in the calf region, and 100% or more in the thigh region. The difference in relative stretch is a primary factor contributing to the large variance of gradient in the pressure profile of the stocking, there being less pressure in areas of greateer lengthwise stretch. The disclosed fabric is capable of producing very rapid changes in the exerted compressive pressure along the length of the leg.

The fabric may be knit using any of a number of knitting machines having a wide range capability. Such machines include the Zodiac 4G manufactured by Billi S.p.A. Firenze Cinstruzione Macchine Tessili of Italy, the Lonati 303 manufactured by Lonati Macchine Circolaci Per Calcifici of Italy, and the Nagata KT-Super 24 manufactured by Nagata Seiki Co., Ltd. of Japan. Such wide-range machines may be ordered new to produce a specified fabric, or existing machines may readily be modified or adapted as required. In general, the modifications required involve needle selection and placement, and cutting the jacks in the correct order.

In other embodiments, the two courses of elastomeric yarn may be knit-tuck rather than knit-float, in which case the fabric will be double rather than single face; courses 1, 3, 4 and 6 may be any of a wide range of desired yarns, including textured filament, flat filament or spun yarn; and courses 2 and 5 may be any desired elastomeric yarn, either bare or covered.

Figure 5:
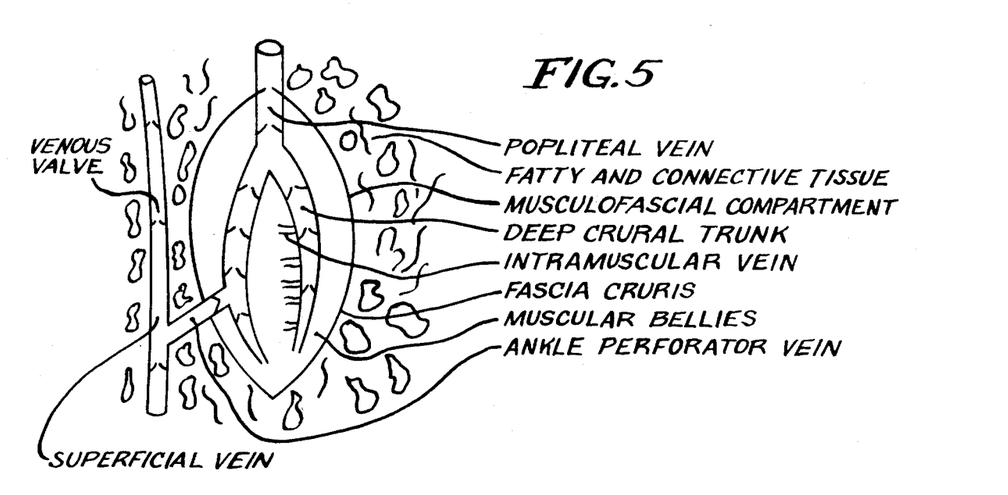
FIG. 5 is a diagrammatic view of a model of a venous pump in a patient's leg.

As a background for the stockings of the present invention, the proper definition of compression profiles requires an understanding of the physiology of the lower extremities for the various venous conditions under consideration as follows: (1) symptomic/yet mild venous disease (tired, aching legs), (2) superficial venous insufficiency, and (3) deep venous insufficiency. The starting point for the definition of the compression profiles will be an analysis of the venous pump as it reflects one model of the mechanism by which blood is drained from the leg in normal physiology in the various pathological conditions. The view of FIG. 5 shows the musculo-venous pump section which provides the anatomical configuration through which the venous pump ejects blood from the lower limb tissue via a dynamic action of the muscle working with/on the venous vessels and in conjunction with the uni-directional venous valves ejects the blood from the tissue.

The action of the venous pump has been divided into three components or phases:

1. Diastole II—the state of slow steady flow prior to muscle contraction in which the blood is flowing through valves at a slow rate.

2. Systole—the state during muscle contraction when pressure in the deep crural veins or trunk rises above that in the popliteal vein, and blood is forced out of the musculofascial compartment. The normal valve function prevents the flow of blood from deep to superficial system at this time, and also prevents the flow of blood in the distal direction of the superficial system.

3. Diastole I—upon cessation of muscle contraction the pressure in the deep system falls suddenly, and the popliteal valve closes to prevent retrograde flow in the deep system.

The valves in the superficial segment or vein close to prevent retrograde flow of blood. Due to the low pressure in the fascia cruris, flow will occur from the superficial to the deep system via the perforator veins. Flow from the muscle tributaries or intramuscular veins will cause the pressure to increase in the central deep vein until the pressure at the popliteal inverts causing the valve to open. At this point the cycle is complete and diastole II begins again.

Figure 6A:
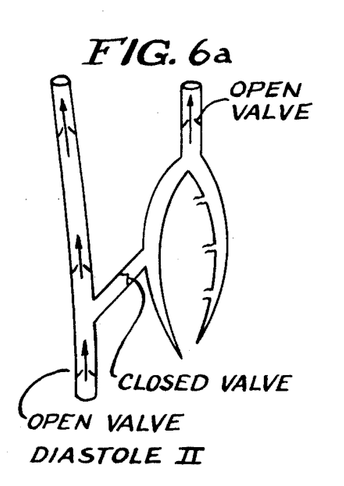
FIGS. 6a-6c are diagrammatic views of the venous pump during three phases of the pump.
Figure 6B:
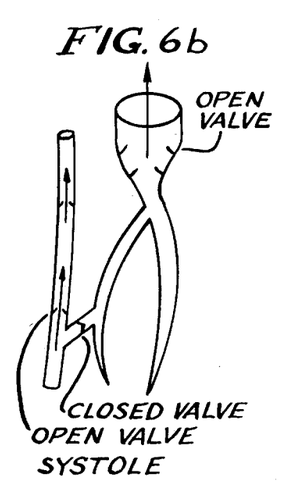
Figure 6C:
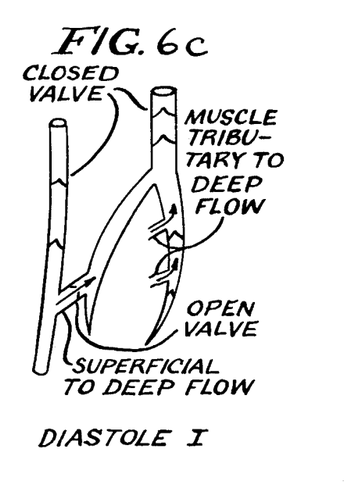

The components of the cycle discussed above are disclosed in FIG. 6 in connection with diastole II, systole, and diastole I.

The above-described function is reflective of a normal venous pump. Due to venous distension and/or venous valve destruction, the various venous pump pathologies arise as a result of loss of valvular function to produce one-way blood flow. In the case of deep venous insufficiency where total deep valvular destruction, such as the popliteal vein or the musculo-fascio compartment, as well as incompetent perforator veins are present, the blood flow pattern changes drammatically over the three phases of venous pump function compared to normal, and results in an inability of the venous pump to reduce the venous pressure during ambulation.

Figure 7A:
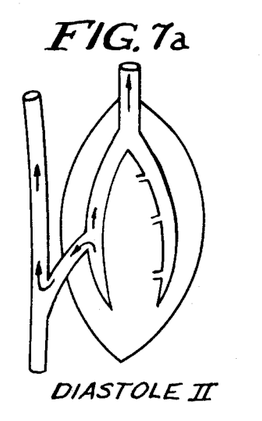
FIGS. 7a-7c are diagrammatic views of different phases of the pump in the case of deep venous insufficiency in the patient's leg.
Figure 7B:
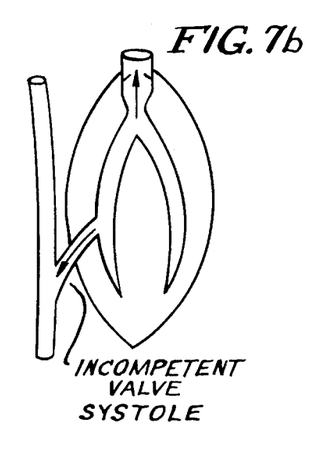
Figure 7C:
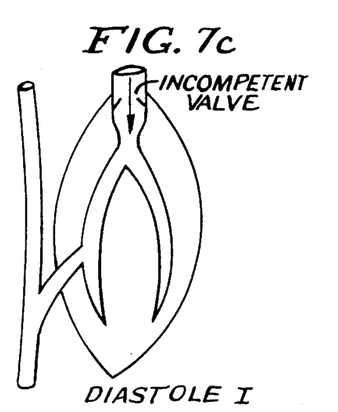

The phases of the cycle for deep venous insufficiency are disclosed in connection with FIG. 7, as follows:

Diastole II—blood flow is driven outward from the deep to superficial system.

Systole—blood flow is driven sharply from deep to superficial, and the flow from the deep trunk veins through the popliteal is compromised.

Diastole I—with cessation of muscular activity and the incompetence of the popliteal valve, blood immediately flows into the deep crural veins.

Figure 8A:
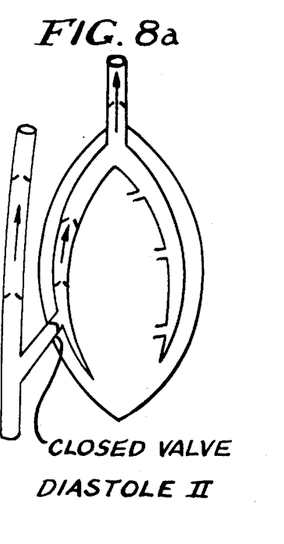
FIGS. 8a-8c are diagrammatic views of different phases of the pump in the case of superficial venous insufficiency in the patient's leg.
Figure 8B:
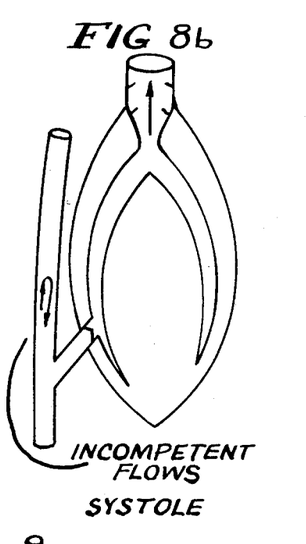
Figure 8C:
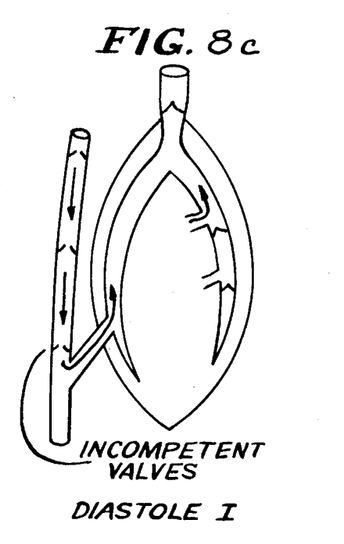

The phases of the cycle for superficial venous insufficiency is disclosed in connection with FIG. 8. In the case of superficial venous insufficiency, the valvular incompetence is present in the superficial vein with the valves in the deep system and the perforators being competent. The phases in this case are discussed as follows:

Diastole II—slow steady flows in the deep as well as the superficial system, and no flow in the perforator due to the closed valve.

Systole—blood is expelled from the deep system through the popliteal; however, due to incompetence of superficial venous valves blood is not effectively expelled from the superficial system, that is, the superficial valves do not produce a one-way flow and result in a nondirectional flow of blood.

Diastole I—popliteal closes due to sudden decrease in pressure within the fascia cruris.

Flow from the superficial system to the deep system occurs via the perforators; however, the superficial system immediately refills to restore high venous pressure.

The nature of both of the above casses of venous disease involves the dysfunction of important venous valves in the proximal (in a direction toward the heart) aspects of the circulation, i.e., the popliteal valve in the case of deep venous insufficiency, and a corresponding valve in the superficial system in the case of superficial venous insufficiency. As a result, the problems are manifest as larger pressure abnormalities in the distal (in a direction away from the heart) regions of the extremity, as well as, abnormalities in more localized regions of the extremity in the small vessel circulation. The abnormalities observed in the distal region of the deep venous circulation in deep venous insufficiency can be measured with pressure transducers. Similarly, the abnormalities observed in the distal region of the superficial venous system in superficial venous insufficiency can be measured with pressure transducers. Both types of abnormalities reflect differences from normal physiology which are large as they are the result of the key venous valve dysfunction, and the impact of the large column of blood under gravity to produce large abnormalities which are easily measured in pressure differences. These differences are also reflected in abnormalities in localized regions of small vessel circulation which can be assessed by photoplethysmography.

The remaining category of venous disease, mild varicose veins by definition is not that different from normal physiology with respect to gross parameters such as venous pressure and yet under certain experimental regimens, abnormalities can be measured in localized regions of small vessel circulation. These changes in venous function could be the result of a number of microscopic hemodynamic conditions such as localized edema in areas surrounding venules.

Figure 9:
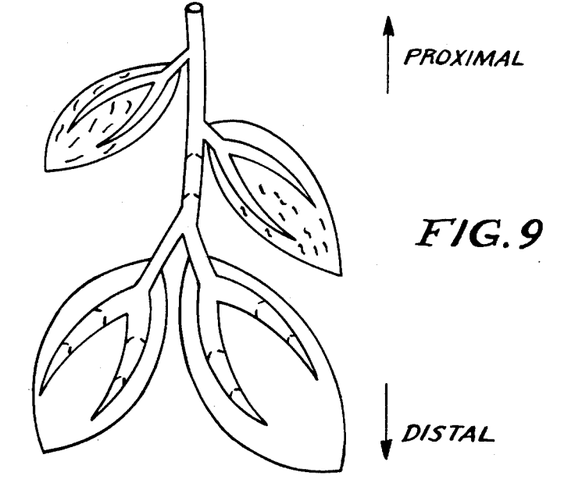
FIG. 9 is a diagrammatic view of the venous pump in a patient's leg.

For each of the disease states the problem can be described in connection with FIG. 9 as follows. For deep venous insufficiency, the proximal portion of the leg has abnormalities in localized microscopic tissue hemodynamics. In the distal portion of the leg, there are some large abnormal pressures in the main trunks of the deep veins, and abnormalities in localized microscopic tissue hemodynamics. For superficial venous insufficiency, in the proximal portion of the leg are found abnormalities in localized microscopic tissue hemodynamics. In the distal portion of the leg, there are found large abnormal pressures in th superficial system, and abnormalities in localized microscopic tissue hemodynamics. In mild venous disease the valves are largely competent. In the proximal portion of the leg, localized microscopic hemodynamics may or may not be present. In the distal portion of the leg, no gross hemodynamic abnormalities are found since the valves are functional. However, under specific workload regimen, localized microscopic abnormalities in tissue are present.

The objectives of the invention for the diseases may be defined as follows:

Deep Venous Insufficiency

| | Distal Requirements |
|---|---|
| 1 | Support deep venous system within muscle to aid venous pump to expel blood during ambulation; |
| 2 | Support deep venous system within leg to aid function to venous valves in reducing retrograde flow during Diastole I. |
| 3 | Support perforating veins to retard flow from deep to superficial during Systole; and |
| 4 | Support small vessel hemodynamics. |
| | Proximal Requirements |
| 1 | Support localized tissue hemodynamics in small vessels of shallow tissue; and |
| 2 | Support of function of venous valves. |

Superficial Venous Insufficiency

| | Distal Requirements |
|---|---|
| 1 | Support superficial venous system to aid venous pump to expel blood during ambulation; |
| 2 | Support superficial venous valves to retard retrograde flow during Diastole I; |
| 3 | In cases of perforator incompetence, support perforators to retard deep to superficial flow during Systole; and |
| 4 | Support small vessel hemodynamics. |
| | Proximal Requirements |
| 1 | Support of venous valves; and |
| 2 | Support of small vessel hemodynamics. |

Mild Venous Disease

| | Distal Requirements |
|---|---|
| 1 | Support small vessel hemodynamics; and |
| 2 | Mild valve support. |
| | Proximal Requirements |
| 1 | Support small vessel hemodynamics; and |
| 2 | Mild valve support. |

All of the above support functions must be accomplished without impeding the outflow parameters of venous blood from the leg or the arterial blood into the leg.

In addition to meeting the above functional objectives for the support of the venous system, it is important for patient compliance to avoid excess forces on the foot, and at the same time avoid venous congestion in the foot which could potentially be produced by a tourniquet effect.

Figure 10:
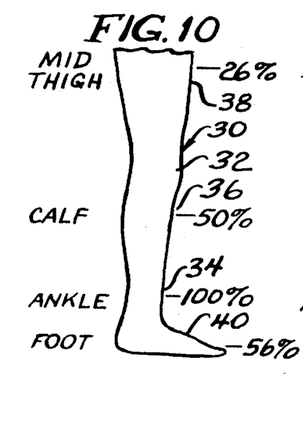
FIG. 10 is an elevational view showing a stocking of the present invention for use with a patient having deep venous insufficiency in the leg.

A full length high compression stocking generally designated 30 for use in connection with deep venous insufficiency in a patient's leg is illustrated in FIG. 10. The stocking 30 has a boot portion 32 for covering a substantial portion of the patient's leg, with the boot portion 32 having an ankle portion 34 for exerting a substantial compressive pressure against the region of the patient's ankle, a calf portion 36 for exerting a compressive pressure in the region of the patient's calf, a thigh portion 38 for exerting a compressive pressure in the region of the patient's thigh, and a foot portion 40 for exerting a compressive pressure in the region of the patient's foot.

The ankle portion 32 is taken as a reference point for compressive pressures of the stocking, and is designated as 100% of the pressure profile. The ankle portion 34 preferably exerts a compressive pressure in the range of 42 to 48 mm of mercury, and preferably approximately 45 mm of mercury. The stocking 30 is designed to support distal veins (deep) through muscle, with the highest pressure being applied by the ankle portion 34 which reduces retrograde flow during systole in the deep as well as the perforator system. Of the three categories of venous disease, the stocking 30 requires the highest pressure in the region of the ankle.

The pressures exerted by other portions of the stocking 30 are designated as being relative to the ankle pressure. As shown, the compressive pressure exerted by the calf portion 36 is approximately 50% of the pressure exerted by the ankle portion 34, and the pressure exerted by the calf portion 36 is in the range of 40% to 60% of the pressure exerted by the ankle portion 34. This large gradient provides a pressure in the calf which supports the microscopic hemodynamics and the valvular function, and yet does not produce venous congestion by resisting venous outflow. This factor is important in producing improved pump efficiency in the leg. The compressive pressure exerted by the calf portion 36 in the region of the calf is in the range of 19.2 mm of mercury to 25.2 mm of mercury, and is preferably approximately 22.5 mm of mercury.

The compressive pressure exerted by the thigh portion 38 in the region of the mid-thigh reflects another large gradient from the calf, and is approximately 26% of the pressure exerted by the ankle portion 34. The thigh pressure is in the range of 16% to 36% of the pressure exerted by the ankle portion 34. The pressure exerted by the thigh portion 38 in the region of the mid-thigh is in the range of 7.7 to 15.1 mm of mercury, and preferably approximately 12 mm of mercury. This pressure in the region of the mid-thigh again reflects support for deep valvular structures and the support of localized microscopic hemodynamics, and yet is low enough to avoid venous congestion.

As shown, the compressive pressure exerted by the foot portion 40 in the region of the foot is approximately 56% of the pressure exerted by the ankle portion 34 in the region of the ankle, and may be in the range of 41% to 71% of the pressure exerted by the ankle portion 34 in the ankle region. The compressive pressure exerted by the foot portion 40 is in the range of 19.7 to 29.8 mm of mercury, and is preferably approximately 25 mm of mercury. The reduced pressure exerted in the foot region 40 is designed to achieve greater patient comfort and enhance application of the stocking 30, while avoiding a tourniquet effect.

Figure 11:
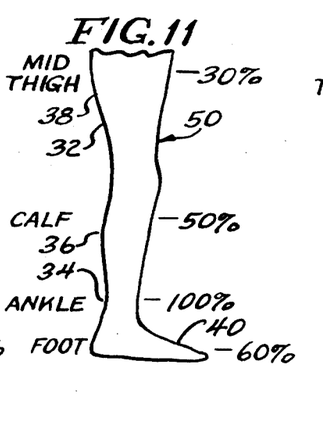
FIG. 11 is an elevational view showing a stocking of the present invention for use with a patient having a superficial venous insufficiency in the leg.

A medium compression stocking generally designated 50 for use in patients having superficial venous insufficiency in the leg is illustrated in FIG. 11, in which like reference numerals designate like parts. The stocking 50 is used for cases of lesser severity than the high compression stocking 30, and has an ankle pressure of less magnitude than the ankle pressure of the high compression stocking 30. As shown, the ankle portion 34 is again taken as a reference for the pressure profile, and is designated as having 100% of the compressive pressure exerted by the stocking 50. The compressive pressure exerted by the ankle portion 34 in the region of the ankle may be in the range of 28 to 32 mm of mercury, and is preferably approximately 30 mm of mercury. The compression in the ankle region is sufficient to retard retrograde flow in the superficial system, and as such also supports the microscopic circulation in the localized area.

As shown, the compressive pressure exerted by the calf portion 36 in the region of the calf is approximately 50% of the compressive pressure exerted by the ankle portion 34 to again support valvular structures and microscopic hemodynamics in this region, but is low enough to avoid venous congestion by retarding outflow of blood. The compressive pressure exerted by the calf portion 36 may be in the range of 40% to 60% of the compressive pressure exerted by the ankle portion 34. The compressive pressure exerted by the calf portion 36 may be in the range of 12.8 to 16.8 mm of mercury, and is preferably approximately 15.0 mm of mercury.

The compressive pressure exerted by the thigh portion 38 in the region of the mid-thigh is approximately 30% of the compressive pressure exerted by the ankle portion 34 to support superficial valvular structures and support localized microscopic hemodynamics without retarding venous outflow. The compressive pressure exerted by the thigh portion 38 in the region of the mid-thigh may be in the range of 20% to 40% of the compressive pressure exerted by the ankle portion 34. The compressive pressure exerted by the thigh portion 38 may be in the range of 6.4 to 11.2 mm of mercury and is preferably approximately 9.0 mm of mercury.

As shown, the pressure exerted by the foot portion 40 in the region of the foot is reduced to 60% of the compressive pressure exerted by the ankle portion 34 in order to achieve greater patient compliance or acceptance without a tourniquet effect. The compressive pressure exerted by the foot portion 40 may be in the range of 45% to 75% of the compressive pressure exerted by the ankle portion 34. Also, the compressive pressure exerted by the foot portion 40 may be in the range of 14.4 to 21.0 mm of mercury, and is preferably approximately 18.0 mm of mercury.

Figure 12:
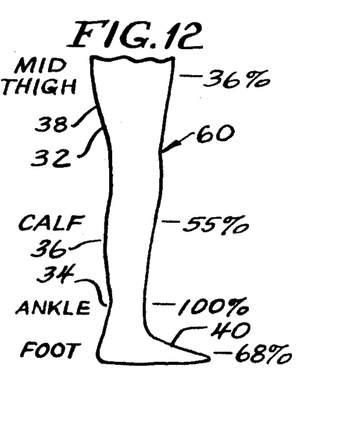
FIG. 12 is an elevational view showing a stocking of the present invention for use with a patient having a mild venous disease in the leg.

A low compression stocking generally designated 60 for treatment of mild venous disease in a patient's leg is illustrated in FIG. 12, in which like reference numerals designate like parts. An important feature of this stocking 60 is the mild support of valvular structure and support of localized microscopic hemodynamics.

Again, the highest pressure in the pressure profile is exerted by the ankle portion 34 in the region of the ankle, and is designated as 100% of the pressure. The pressure exerted by the ankle portion 34 may be in the range of 20 to 24 mm of mercury, and is preferably approximately 22 mm of mercury.

As shown, the compressive pressure exerted by the calf portion 36 in the region of the calf is preferably approximately 55% of the compressive pressure exerted by the ankle portion 34 in order to provide support and yet avoid venous congestion. The compressive pressure exerted by the calf portion 36 may be in the range of 45% to 65% of the compressive pressure exerted by the ankle portion 34. The compressive pressure exerted by the calf portion 36 may be in the range of 10.8 to 13.0 mm of mercury, and is preferably approximately 12.0 mm of mercury.

The compressive pressure exerted by the thigh portion 38 in the region of the mid-thigh is preferably approximately 36% of the compressive pressure exerted by the ankle portion 34 to provide microvascular support and complement valvular function without interfering with venous outflow. The compressive pressure exerted by the thigh portion 38 in the region of the mid-thigh may be in the range of 27% to 45% of the compressive pressure exerted by the ankle portion 34. The compressive pressure exerted by the thigh portion 38 may be in the range of 6.5 to 9.0 mm of mercury, and is preferably approximately 8.0 mm of mercury.

As shown, the pressure exerted by the foot portion 40 in the region of the foot is relieved to approximately 68% of the compressive pressure exerted by the ankle portion 34 in order to enhance application of the stocking 60 and comfort to the patient while avoiding tourniquet effects. The compressive pressure exerted by the foot portion 40 may be in the range of 53% to 83% of the compressive pressure exerted by the ankle portion 34. The compressive pressure exerted by the foot portion 40 may be in the range of 12.7 to 16.6 mm of mercury, and is preferably approximately 15.0 mm of mercury.

In all three types of the stockings 30, 50, and 60, the pressure in the foot portion 40 is reduced relative to the pressure exerted by the ankle portion 34. Since the foot is a bony structure excess pressures exerted on the foot would tend to break down the soft tissue in the foot resulting in damage to the soft foot tissue, such as the instep, or squeezing of the toes. The relieved foot pressures in the stockings of the invention minimize the possibility of this result.

Also, in all three types of the stockings 30, 50, and 60, with an appropriate sizing system consistent with the general population, a meaningful pressure gradient is always maintained with an acceptable number of sizes. This aspect of the invention is a key to physiological function, and is not achieved with a majority of ambulatory stockings in today's marketplace.

The foregoing detailed description is given for clearness of understanding only, and no unnecessary limitations should be understood therefrom, as modifications will be obvious to those skilled in the art.

We claim:

1. A therapeutic stocking for deep venous insufficiency of the leg comprising, a boot portion for covering a substantial portion of the leg, said boot portion having an ankle portion for exerting a substantial compressive pressure against the region of the ankle, a calf portion for exerting approximately 50% of the compressive pressure exerted by the ankle portion in the region of the calf, and a thigh portion for exerting approximately 26% of the compressive pressure exerted by the ankle portion in the region of the mid-thigh.

2. The stocking of claim 1 including a foot portion which exerts approximately 56% of the compressive pressure exerted by the ankle portion in the region of the foot.

3. The stocking of claim 1 wherein the ankle portion exerts a compressive pressure of approximately 45 mm of mercury against the region of the ankle.

4. The stocking of claim 1 wherein the ankle portion exerts a compressive pressure in the range of 42 to 48 mm of mercury against the region of the ankle.

5. A therapeutic stocking for superficial venous insufficiency of the leg comprising, a boot portion for covering a substantial portion of the leg, said boot portion having an ankle portion for exerting a substantial compressive pressure against the region of the ankle, a calf portion for exerting approximately 50% of the compressive pressure exerted by the ankle portion in the region of the calf, and a thigh portion for exerting approximately 30% of the compressive pressure exerted by the ankle portion in the region of the mid-thigh.

6. The stocking of claim 5 including a foot portion which exerts approximately 60% of the compressive pressure exerted by the ankle portion in the region of the foot.

7. The stocking of claim 5 wherein the ankle portion exerts a compressive pressure of approximately 30 mm of mercury against the region of the ankle.

8. The stocking of claim 5 wherein the ankle portion exerts a compressive pressure in the range of 28 to 32 mm of mercury against the region of the ankle.

9. A therapeutic stocking for mild venous disease of the leg comprising, a boot portion for covering a substantial portion of the leg, said boot portion having an ankle portion for exerting a substantial compressive pressure against the region of the ankle, a calf portion for exerting approximately 55% of the compressive pressure exerted by the ankle portion in the region of the calf, and a thigh portion for exerting approximately 36% of the compressive pressure exerted by the ankle portion in the region of the mid-thigh.

10. The stocking of claim 9 including a foot portion which exerts approximately 68% of the compressive pressure exerted by the ankle portion in the region of the foot.

11. The stocking of claim 9 wherein the ankle portion exerts a compressive pressure of approximately 22 mm of mercury against the region of the ankle.

12. The stocking of claim 9 wherein the ankle portion exerts a compressive pressure in the range of 20 to 24 mm of mercury against the region of the ankle.

13. A therapeutic stocking for deep venous insufficiency of the leg comprising, a boot portion for covering a substantial portion of the leg, said boot portion having an ankle portion for exerting a substantial compressive pressure against the region of the ankle, a calf portion for exerting a compressive pressure in the range of 40% to 60% of the ankle pressure in the region of the calf, and a thigh portion for exerting a compressive pressure in the range of 16% to 36% of the ankle pressure in the region of the mid-thigh.

14. The stocking of claim 13 including a foot portion which exerts a compressive pressure in the range of 41% to 71% of the ankle pressure in the region of the foot.

15. The stocking of claim 13 wherein the ankle portion exerts a compressive pressure of approximately 45 mm of mercury against the region of the ankle.

16. The stockings of claim 13 wherein the ankle portion exerts a compressive pressure in the range of 42 to 48 mm of mercury against the region of the ankle.

17. A therapeutic stocking for superficial venous insufficiency of the leg comprising, a boot portion for covering a substantial portion of the leg, said boot portion having an ankle portion for exerting a substantial compressive pressure against the region of the ankle, a calf portion for exerting a compressive pressure in the range of 40% to 60% of the ankle pressure in the region of the calf, and a thigh portion for exerting a compressive pressure in the range of 20% to 40% of the ankle pressure in the region of the mid-thigh.

18. The stocking of claim 17 including a foot portion which exerts a compressive pressure in the range of 45% to 75% of the ankle pressure in the region of the foot.

19. The stocking of claim 17 wherein the ankle portion exerts a compressive pressure of approximately 30 mm of mercury against the region of the ankle.

20. The stocking of claim 17 wherein the ankle portion exerts a compressive pressure in the range of 28 to 32 mm of mercury against the region of the ankle.

21. A therapeutic stocking for mild venous disease of the leg comprising, a boot portion for covering a substantial portion of the leg, said boot portion having an ankle portion for exerting a substantial compressive pressure against the region of the ankle, a calf portion for exerting a compressive pressure in the range of 45% to 65% of the ankle pressure in the region of the calf, and a thigh portion for exerting a compressive pressure in the range of 27% to 45% of the ankle pressure in the region of the mid-thigh.

22. The stocking of claim 21 including a foot portion which exerts a compressive pressure in the range of 53% to 83% of the ankle pressure in the region of the foot.

23. The stocking of claim 21 wherein the ankle portion exerts a compressive pressure of approximately 22 mm of mercury against the region of the ankle.

24. The stocking of claim 21 wherein the ankle portion exerts a compressive pressure in the range of 20 to 24 mm of mercury in the region of the ankle.

25. A therapeutic stocking for deep venous insufficiency of the leg comprising, a boot portion for covering a substantial portion of the leg, said boot portion having an ankle portion which exerts a compressive pressure of approximately 45 mm of mercury in the region of the ankle, a calf portion which exerts a compressive pressure of approximately 22.5 mm of mercury in the region of the calf, and a thigh portion which exerts a compressive pressure of approximately 12 mm of mercury in the region of the mid-thigh.

26. The stocking of claim 25 including a foot portion which exerts a compressive pressure of approximately 25 mm of mercury in the region of the foot.

27. A therapeutic stocking for superficial venous insufficiency of the leg comprising, a boot portion for covering a substantial portion of the leg, said boot portion having an ankle portion which exerts a compressive pressure of approximately 30 mm of mercury in the region of the ankle, a calf portion which exerts a compressive pressure of approximately 15 mm of mercury in the region of the calf, and a thigh portion which exerts a compressive pressure of approximately 9 mm of mercury in the region of the mid-thigh.

28. The stocking of claim 27 including a foot portion which exerts a compressive pressure of approximately 18 mm of mercury in the region of the foot.

29. A therapeutic stocking for mild venous disease of the leg comprising, a boot portion for covering a substantial portion of the leg, said boot portion having an ankle portion which exerts a compressive pressure of approximately 22 mm of mercury in the region of the ankle, a calf portion which exerts a compressive pressure of approximately 12 mm of mercury in the region of the calf, and a thigh portion which exerts a compressive pressure of approximately 8 mm of mercury in the region of the mid-thigh.

30. The stocking of claim 29 including a foot portion which exerts a compressive pressure of approximately 15 mm of mercury in the region of the foot.

31. A therapeutic stocking for deep venous insufficiency of the leg comprising, a boot portion for covering a substantial portion of the leg, said boot portion having an ankle portion which exerts a compressive pressure in the range of 42 to 48 mm of mercury in the region of the ankle, a calf portion which exerts a compressive pressure in the range of 19.2 to 25.2 mm of mercury in the region of the calf, and a thigh portion which exerts a compressive pressure in the range of 7.7 to 15.1 mm of mercury in the region of the mid-thigh.

32. The stocking of claim 31 including a foot portion which exerts a compressive pressure in the range of 19.7 to 29.8 mm of mercury in the region of the foot.

33. A therapeutic stocking for superficial venous insufficiency of the leg comprising, a boot portion for covering a substantial portion of the leg, said boot portion having an ankle portion which exerts a compressive pressure in the range of 28 to 32 mm of mercury in the region of the ankle, a calf portion which exerts a compressive pressure in the range of 12.8 to 16.8 mm of mercury in the region of the calf, and a thigh portion which exerts a compressive pressure in the range of 6.4 to 11.2 mm of mercury in the region of the mid-thigh.

34. The stocking of claim 33 including a foot portion which exerts a compressive pressure in the range of 14.4 to 21.0 mm of mercury in the region of the foot.

35. A stocking for mild venous disease of the leg comprising, a boot portion for covering a substantial portion of the leg, said boot portion having an ankle portion which exerts a compressive pressure in the range of 20 to 24 mm of mercury in the region of the ankle, a calf portion which exerts a compressive pressure in the range of 10.8 to 13.0 mm of mercury in the region of the calf, and a thigh portion which exerts a compressive pressure in the range of 6.5 to 9.0 mm of mercury in the region of the mid-thigh.

36. The stocking of claim 35 including a foot portion which exerts a compressive pressure in the range of 12.7 to 16.6 mm of mercury in the region of the foot.

37. A therapeutic stocking for deep venous insufficiency of the leg comprising, an ankle portion for exerting a substantial compressive pressure against the region of the ankle, and a foot portion which exerts approximately 56% of the compressive pressure exerted by the ankle portion in the region of the foot.

38. The stocking of claim 37 wherein the ankle portion exerts a compressive pressure of approximately 45 mm of mercury against the region of the ankle.

39. A therapeutic stocking for superficial venous insufficiency of the leg comprising, an ankle portion for exerting a substantial compressive pressure against the region of the ankle, and a foot portion which exerts approximately 60% of the compressive pressure exerted by the ankle portion in the region of the foot.

40. The stocking of claim 30 wherein the ankle portion exerts a compressive pressure of approximately 30 mm of mercury against the region of the ankle.

41. A therapeutic stocking for mild venous disease of the leg comprising, an ankle portion for exerting a substantial compressive pressure against the region of the ankle, and a foot portion which exerts approximately 68% of the compressive pressure exerted by the ankle portion in the region of the foot.

42. The stocking of claim 41 wherein the ankle portion exerts a compressive pressure of approximately 22 mm of mercury against the region of the ankle.

43. A therapeutic stocking for deep venous insufficiency of the leg comprising, an ankle portion for exerting a substantial compressive pressure against the region of the ankle, and a foot portion which exerts a compressive pressure in the range of 41% to 71% of the ankle pressure in the region of the foot.

44. The stocking of claim 43 wherein the ankle portion exerts a compressive pressure of approximately 45 mm of mercury against the region of the ankle.

45. A therapeutic stocking for superficial venous insufficiency of the leg comprising, an ankle portion for exerting a substantial compressive pressure against the region of the ankle, and a foot portion which exerts a compressive pressure in the range of 45% to 75% of the ankle pressure in the region of the foot.

46. The stocking of claim 45 wherein the ankle portion exerts a compressive pressure of approximately 30 mm of mercury against the region of the ankle.

47. A therapeutic stocking for mild venous disease of the leg comprising, an ankle portion for exerting a substantial compressure pressure against the region of the ankle, and a foot portion which exerts a compressive pressure in the range of 53% to 83% of the ankle pressure in the region of the foot.

48. The stocking of claim 47 wherein the ankle portion exerts a compressive pressure of aproximately 22 mm of mercury against the region of the ankle.

49. A therapeutic stocking for deep venous insufficiency of the leg comprising, an ankle portion which exerts a compressive pressure of approximately 45 mm of mercury in the region of the ankle, and a foot portion which exerts a compressive pressure of approximately 25 mm of mercury in the region of the foot.

50. A therapeutic stocking for superficial venous insufficiency of the leg comprising, an ankle portion which exerts a compressive pressure of approximately 30 mm of mercury in the region of the ankle, and a foot portion which exerts a compressive pressure of approximately 18 mm of mercury in the region of the foot.

51. A therapeutic stocking for mild venous disease of the leg comprising, an ankle portion which exerts a compressive pressure of approximately 22 mm of mercury in the region of the ankle, and a foot portion which exerts a compressive pressure of approximately 15 mm of mercury in the region of the foot.

52. A therapeutic stocking for deep venous insufficiency of the leg comprising, an ankle portion which exerts a compressive pressure in the range of 42 to 48 mm of mercury in the region of the ankle, and a foot portion which exerts a compressive pressure in the range of 19.7 to 29.8 mm of mercury in the region of the foot.

53. A therapeutic stocking for superficial venous insufficiency of the leg comprising, an ankle portion which exerts a compressive pressure in the range of 28 to 32 mm of mercury in the region of the ankle, and a foot portion which exerts a compressive pressure in the range of 14.4 to 21.0 mm of mercury in the region of the foot.

54. A stocking for mild venous disease of the leg comprising, an ankle portion which exerts a compressive pressure in the range of 20 to 24 mm of mercury in the region of the ankle, and a foot portion which exerts a compressive pressure in the range of 12.7 to 16.6 mm of mercury in the region of the foot.

* * * * *